(12) United States Patent
Chung et al.

(10) Patent No.: US 8,236,509 B2
(45) Date of Patent: Aug. 7, 2012

(54) METHOD FOR PREPARING ANTIBODY MONOLAYERS WHICH HAVE CONTROLLED ORIENTATION USING PEPTIDE HYBRID

(75) Inventors: Sang Jeon Chung, Taejeon-si (KR); Bong Hyun Chung, Taejeon-si (KR); Yongwon Jung, Taejeon-si (KR); Hyo Jin Kang, Pohang-si (KR); Jeong Min Lee, Taejeon-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 211 days.

(21) Appl. No.: 12/679,982

(22) PCT Filed: Oct. 18, 2007

(86) PCT No.: PCT/KR2007/005106
§ 371 (c)(1),
(2), (4) Date: Mar. 25, 2010

(87) PCT Pub. No.: WO2009/044949
PCT Pub. Date: Apr. 9, 2009

(65) Prior Publication Data
US 2010/0209945 A1 Aug. 19, 2010

(30) Foreign Application Priority Data
Oct. 1, 2007 (KR) .................. 10-2007-0098852

(51) Int. Cl.
*G01N 33/53* (2006.01)
(52) U.S. Cl. .................. 435/7.1; 435/7.2; 436/518
(58) Field of Classification Search .................. None
See application file for complete search history.

(56) References Cited

U.S. PATENT DOCUMENTS

| | | | |
|---|---|---|---|
| 5,463,026 A * | 10/1995 | Nakamura et al. | 530/387.9 |
| 2003/0100127 A1 | 5/2003 | Corn et al. | |
| 2004/0253247 A1 * | 12/2004 | Dennis et al. | 424/178.1 |
| 2005/0009206 A1 | 1/2005 | Mirkin et al. | |
| 2006/0153834 A1 * | 7/2006 | Carbonell et al. | 424/133.1 |
| 2006/0252094 A1 | 11/2006 | Zhou et al. | |

OTHER PUBLICATIONS

Blawas, et al., "Protein patterning.", Biomaterials, 19:595-609, 1998.
Nisnevitch, et al., "The solid phase in affinity chromatography: strategies for antibody attachment.", J. Biochem. Biophys. Methods, 49:467-480, 2001.
Danczyk, et al., "Comparison of antibody functionality using different immobilization methods.", Biotechnology and Bioengineering, 84(2), 2003.
Lee, et al., "Direct immobilization of protein G variants with various numbers of cysteine residues on a gold surface.", Anal. Chem., 79:2680-2687, 2007.
Fowler, et al., "Self-assembled layer of thiolated immunosensor scaffold.", Anal. Chem., 79:350-354, 2007.
Lee, et al., "ProteoChip: A highly sensitive protein microarray prepared by a novel method of protein immobilization for application of protein-protein interaction studies.", Proteomics, 3:2289-2304, 2003.
Vega, et al., "Functional antibody arrays through metal Ion-affinity templates.", Chem. Bio. Chem., 7:1653-1657, 2006.
Delano, et al., "Convergent solutions to binding at a protein-protein interface.", Science, 287:1279, 2000.
Yang, et al., "Hexamer peptide affinity resins that bind the Fc region of human immunoglobulin G.", J. Peptide Res., 66(Suppl. 1):120-137, 2006.
Fassina, et al., "Immunoglobulin specificity of TG19318: a novel synthetic ligand for antibody affinity purification.", Journal of Molecular Recognition, 11:128-133, 1998.
Gobi, et al., "Self-assembled PEG monolayer based SPR immunosensor for label-free detection of insulin.", Biosensors and Bioelectronics, 22:1382-1389, 2007.
Gobi, et al., "Enhanced sensitivity of self-assembled monolayer based surface plasmon resonance (SPR) immunosensor for detection of benzaldehyde using single-step multi-sandwich immunoassay.", Anal & Bioanal. Chem., 387:2727-2735, 2007.

* cited by examiner

*Primary Examiner* — Jacob Cheu
(74) *Attorney, Agent, or Firm* — Lucas & Mercanti, LLP

(57) ABSTRACT

The present invention relates to a method for preparing an protein monolayer using a peptide hybrid for protein immobilization, more precisely a peptide hybrid for protein immobilization which has improved solubility by introducing a PEG linker and a proper reaction group to the oligopeptide having specific affinity to selected types of proteins and is designed to provide enough space between solid substrates and proteins immobilized, whereby various solid substrates treated by the hybrid catch specific proteins effectively on. The peptide hybrid for protein immobilization of the present invention facilitates the control of orientation of an antibody on various solid surfaces and immobilization of various antibodies of different origins or having different isotypes with different affinity. Therefore, the surface treatment technique using the peptide hybrid of the invention can be effectively used for the production of various immunosensors and immune chips.

6 Claims, 8 Drawing Sheets

SEQUENCE LISTING

```
<160> NUMBER OF SEQ ID NOS: 6

<210> SEQ ID NO 1
<211> LENGTH: 15
<212> TYPE: PRT
<213> ORGANISM: Artificial Sequence
<220> FEATURE:
<223> OTHER INFORMATION: the partial structures of the peptide hybrids
      represented by formulas 1
<220> FEATURE:
<221> NAME/KEY: DISULFID
<222> LOCATION: (4)..(5)
<220> FEATURE:
<221> NAME/KEY: DISULFID
<222> LOCATION: (14)..(15)

<400> SEQUENCE: 1
```

```
Asp Asp Asp Cys Ala Trp His Leu Gly Glu Leu Val Trp Cys Thr
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: the partial structures of the peptide hybrids
      represented by formulas 1
<220> FEATURE:
<221> NAME/KEY: DISULFID
<222> LOCATION: (4)..(5)
<220> FEATURE:
<221> NAME/KEY: DISULFID
<222> LOCATION: (14)..(15)

<400> SEQUENCE: 2

Asp Glu Asp Cys Ala Trp His Leu Gly Glu Leu Val Trp Cys Thr
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: the partial structures of the peptide hybrids
      represented by formulas 1
<220> FEATURE:
<221> NAME/KEY: DISULFID
<222> LOCATION: (4)..(5)
<220> FEATURE:
<221> NAME/KEY: DISULFID
<222> LOCATION: (14)..(15)

<400> SEQUENCE: 3

Glu Glu Asp Cys Ala Trp His Leu Gly Glu Leu Val Trp Cys Thr
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: the partial structures of the peptide hybrids
      represented by formulas 1
<220> FEATURE:
<221> NAME/KEY: DISULFID
<222> LOCATION: (4)..(5)
<220> FEATURE:
<221> NAME/KEY: DISULFID
<222> LOCATION: (14)..(15)

<400> SEQUENCE: 4

Glu Asp Asp Cys Ala Trp His Leu Gly Glu Leu Val Trp Cys Thr
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: the partial structures of the peptide hybrids
      represented by formulas 1

<400> SEQUENCE: 5

Arg Thr Tyr Arg Thr Tyr Arg Thr Tyr Arg Thr Tyr Lys Lys Lys Gly
1               5                   10                  15

<210> SEQ ID NO 6
```

```
<211> LENGTH: 8
<212> TYPE: PRT
<213> ORGANISM: Artificial Sequence
<220> FEATURE:
<223> OTHER INFORMATION: the partial structures of the peptide hybrids
      represented by formulas 1

<400> SEQUENCE: 6

Gly His Trp Arg Gly Trp Val Ser
1               5
```

METHOD FOR PREPARING ANTIBODY MONOLAYERS WHICH HAVE CONTROLLED ORIENTATION USING PEPTIDE HYBRID

CROSS-REFERENCE TO RELATED APPLICATIONS

This application is a 371 of PCT/KR2007/005106 filed on Oct. 18, 2007, which claims the benefit of Korean Patent Application No. 10-2007-0098852 filed on Oct. 1, 2007, the contents of each of which are incorporated herein by reference.

TECHNICAL FIELD

The present invention relates to a method for preparing an protein monolayer using a peptide hybrid for protein immobilization, more precisely a peptide hybrid for protein immobilization which has improved solubility by introducing a PEG linker and a proper reaction group to the oligopeptide having specific affinity to selected types of proteins and is designed to provide enough space between solid substrates and proteins immobilized, whereby various solid substrates treated by the hybrid catch specific proteins effectively on.

BACKGROUND ART

Antibodies have been immobilized on the surfaces of various inorganic solid materials for producing immunosensor, protein chip, diagnostic kit, etc. The technique to regulate orientation in order to expose the antigen binding site of an antibody on the surface without damaging the activity and binding capacity peculiar to the antibody and thus to immobilize the antibody on the various solid substrates as a form of monolayer is very important since it is directly involved in the detecting sensitivity of a sensor or a chip.

The conventional methods to immobilize an antibody on the surface of a solid substrate rely on physical adsorption or covalent bond formation of a protein. However, the immobilization of an antibody by the conventional methods has disadvantages of protein denaturation, random orientation, decreased binding capacity of the immobilized antibody to the target antigen resulting from random chemical modifications.

To overcome the above problems, antibody immobilization techniques have been developed by using microorganism-originated antibody binding proteins (protein A, protein G, protein A/G or protein L) binding specifically to the corresponding antibody. These proteins bind strongly to a specific region of an antibody that is not involved in the antigen-antibody reaction, immobilizing the antibody on a solid substrate to allow the approach of an antigen. The interaction between the above proteins and antibodies does not require any chemical modification process, suggesting that the unique antibody functions are not damaged. However, it is very difficult to regulate orientation of the proteins during immobilization on a solid substrate, and as a result, the antibody immobilization efficiency might be reduced. Recent studies have been focused on the modification of an antibody binding protein by genetic engineering and chemical approaches to overcome the above problem.

The antibody immobilization using an antibody binding protein has many advantages, compared with the method based on physical adsorption, but still has a problem of protein denaturation by many environmental factors including physical and chemical factors, suggesting that long-term storage is difficult. It is also almost impossible to treat a specific target region only in case a chemical modification is necessary in a specific region of a protein. It is an urgent request, to overcome such problems, to develop a novel method for antibody immobilization using a low molecular weight material having high stability and facilitating immobilization on a solid substrate. Antibody immobilization methods have been developed using a dendrimer, iron ion or calixcrown derivatives, but these methods do not have the control of orientation and selectivity, suggesting that the antibody does not have protein specificity, that is it can be bound to almost every proteins with similar binding capacity which is though not very strong.

To screen a novel low molecular substance for protein immobilization in order to overcome the disadvantages of the conventional antibody binding protein or low molecular substance for antibody immobilization, the present inventors carried out wide document analysis to investigate which low molecular substance could be used as an adsorption material for antibody separation and as a therapeutic agent based on antibody binding. The present inventors selected three kinds of peptides binding selectively to IgG as candidates for the low molecular substance of the invention (DeLano W L et al., *Science* 287:1279-1283, 2000; Yang H et al., *J Peptide Res* 66(Suppl. 1):120-137, 2006; Fassina G et al., *J Mol Recognit* 11:128-133, 1998), and prepared peptide hybrids for protein immobilization by modifying chemical structures of the peptides, and finally completed this invention by confirming that the peptide hybrids for protein immobilization had binding capacity about antibody and antigen on the solid substrate for the immunosensor and antibody chip.

DISCLOSURE

Technical Problem

It is an object of the present invention to provide a bio-chip or an immunosensor with satisfactory surface regularity by inhibiting non-specific binding reaction on the solid substrate during antibody immobilization and by regulating antibody orientation.

Technical Solution

To achieve the above object, the present invention provides a peptide hybrid for protein immobilization composed of an oligopeptide comprising 7-17 amino acids having a specific protein specific affinity and PEG linked to the oligopeptide by covalent bond.

The present invention also provides a method for preparing a protein monolayer comprising the following steps:

1) activating the carboxyl group included in a solid substrate;

2) surface-treating the solid substrate having the activated carboxyl group by adhering the peptide hybrid for protein immobilization of the present invention onto the surface; and, 3) binding a protein onto the surface-treated solid substrate of step 2), and a substrate for protein immobilization surface-treated with the peptide hybrid for protein immobilization of the invention prepared by the same.

The present invention further provides an immunosensor having an antibody immobilized via the peptide hybrid on the solid substrate surface-treated with the peptide hybrid for protein immobilization of the invention.

The present invention also provides a detection method of an antigen comprising the step of detecting the antigen-antibody reaction after adding the sample antigen to the antibody immobilized on the immunosensor.

In addition, the present invention provides a detection method of an antibody in the sample, comprising the following steps:

1) adding an antigen binding specifically to the antibody immobilized on the immunosensor and washing thereof;
2) adding a sample to the washed immunosensor of step 1) and washing thereof; and,
3) detecting the antigen-antibody reaction between the added antigen and the immobilized antibody.

Advantageous Effect

The peptide hybrid for protein immobilization of the present invention provides orientation to an antibody on various types of solid substrate surfaces and facilitates the immobilization of antibodies with different affinities according to their origins or subtypes. Thus, the surface treatment technique using the peptide hybrid of the invention can be effectively used for the production of various immunosensors and immune chips.

DESCRIPTION OF DRAWINGS

The application of the preferred embodiments of the present invention is best understood with reference to the accompanying drawings, wherein.

MODE FOR INVENTION

Hereinafter, the present invention is described in detail.

The present invention provides a peptide hybrid for protein immobilization composed of an oligopeptide comprising 7-17 amino acids having a specific protein specific affinity and PEG linked to the oligopeptide by covalent bond.

The protein herein can be any protein accepted by those in the art, in particular a protein having biological activity selected from the group consisting of proteins for medicinal purpose, research and industry, for example, antigen, antibody, cell receptor, enzyme, structural protein, serum, and cellular protein, and more preferably an antibody. If the protein is an antibody, the oligopeptide has an affinity to Fc of the antibody.

The peptide hybrid for protein immobilization of the invention is preferably composed of 7-17 amino acids for the control of orientation during the protein immobilization on various solid surfaces, and more preferably composed of 13-17 amino acids. The peptide can contain amino acid sequences represented by SEQ. ID. NO: 1-NO: 5 included in the partial structures of the peptide hybrids represented by formulas 1-3 and formula 4 (SEQ. ID. NO: 1: DDDC*AWHLGELVWC*T; SEQ. ID. NO: 2: DEDC*AWHLGELVWC*T; SEQ. ID. NO: 3: EEDC*AWHLGELVWC*T; SEQ. ID. NO: 4: EDDC*AWHLGELVWC*T; formula 4: $(RTY)_4K_2KG$; SEQ. ID. NO 5: GHWRGWVS, C*: disulfide bond) (see Table 1). These peptides are known to bind to Fc site of human immunoglobulin G (DeLano W L et al., *Science* 287:1279-1283, 2000; Yang H et al., *J Peptide Res* 66(Suppl. 1):120-137, 2006; Fassina G et al., *J Mol Recognit* 11:128-133, 1998).

Formula 1

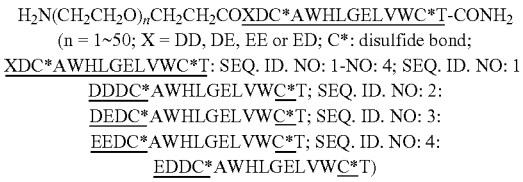

Formula 2

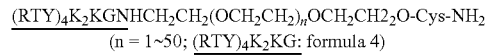

Formula 3

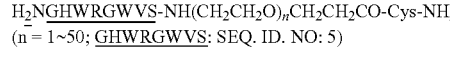

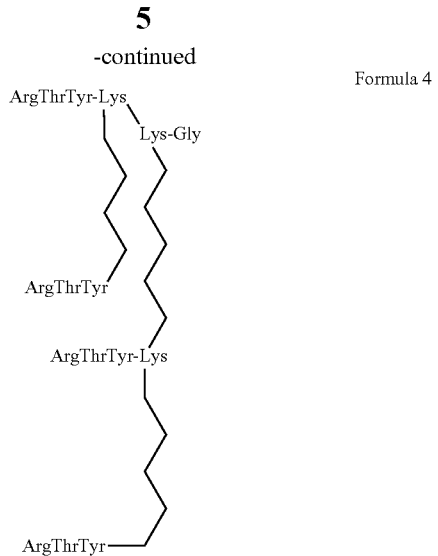

Formula 4

Figure 1:
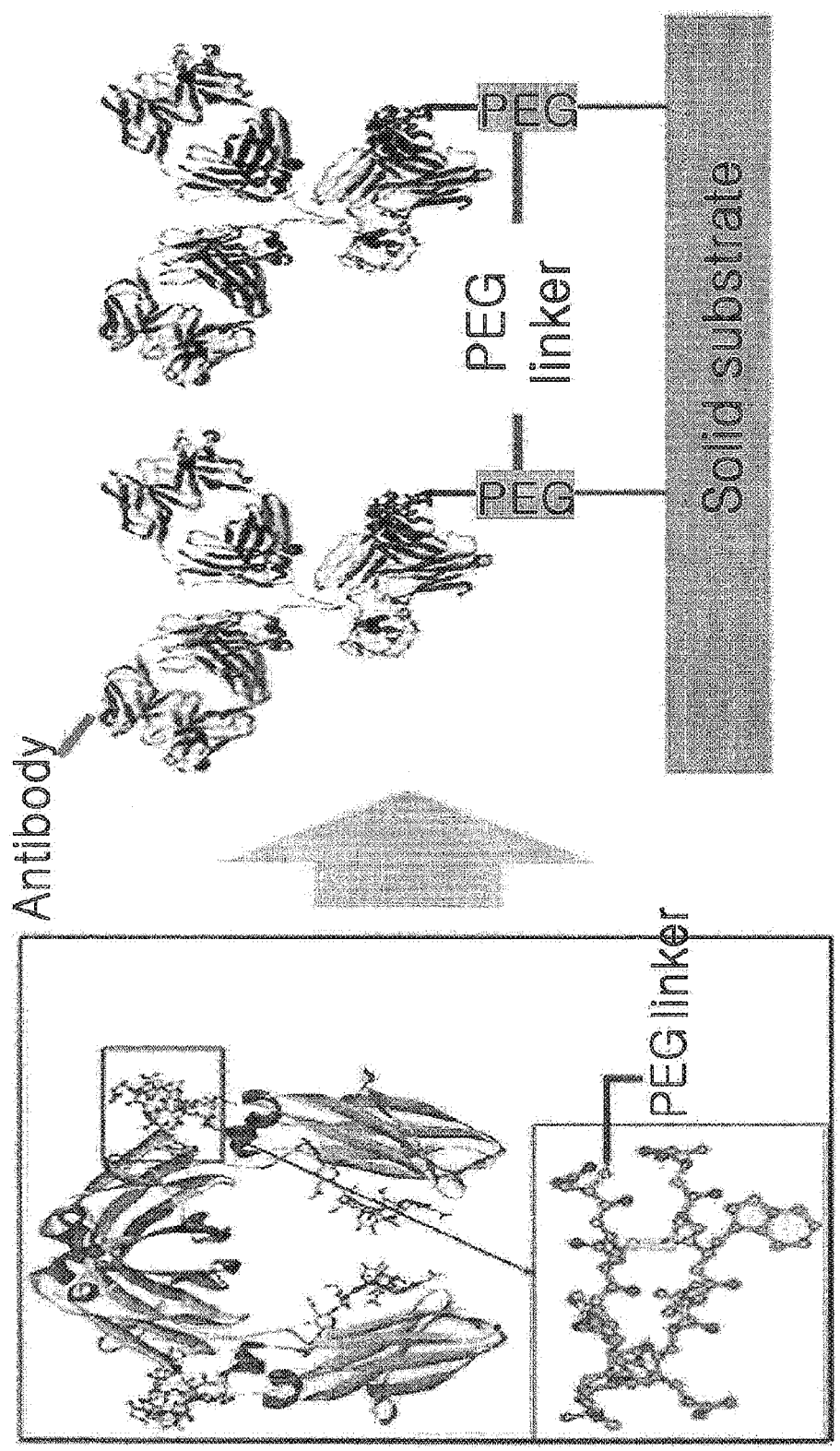
FIG. 1 is a schematic diagram illustrating the principle of antibody immobilization on a solid substrate by the peptide hybrid for protein immobilization of the present invention.

The preferable molecular weight of the PEG (poly ethylene glycol) is 60-3000. The peptide hybrid designed to have the PEG can have improved solubility in a buffer solution and can provide enough space necessary for the effective antibody binding in between the solid substrate and the peptide having the amino acid sequence selected from the group consisting of sequences represented by SEQ. ID. NO: 1-NO: 5 and represented by formula 4 (see FIG. 1).

The peptide hybrid for protein immobilization of the present invention allows various chemical modifications and is preferably one of the peptide hybrids represented by formulas 1-3 containing the peptide having the amino acid sequence selected from the group consisting of sequences represented by SEQ. ID. NO: 1-NO: 5 and formula 4 shown in Table 1, and is more preferably the peptide hybrid represented by formula 1a comprising the peptide having the amino acid sequence represented by SEQ. ID. NO: 4.

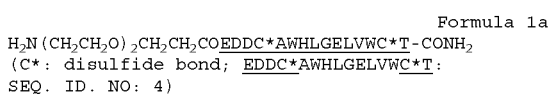

Formula 1a
H$_2$N(CH$_2$CH$_2$O)$_2$CH$_2$CH$_2$COEDDC*AWHLGELVWC*T-CONH$_2$
(C*: disulfide bond; EDDC*AWHLGELVWC*T: SEQ. ID. NO: 4)

Figure 2:
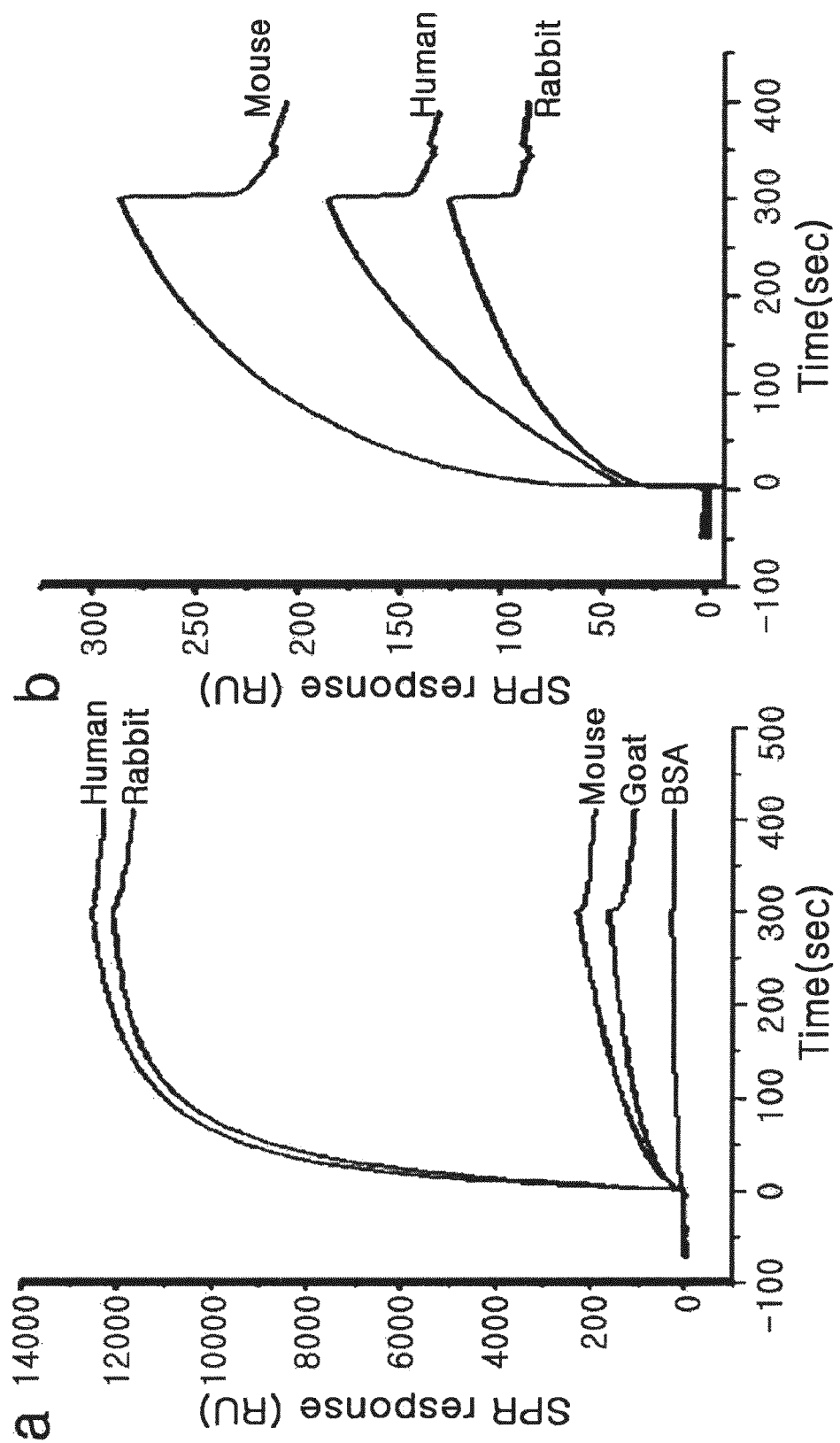
FIG. 2 is a set of graphs illustrating the binding capacities of human, rabbit, mouse and goat antibodies and BSA to the dextran CM-5 Au sensor chip surface-treated with the peptide hybrid for protein immobilization of the invention measured by surface plasmon resonance:
   a: results on the chip surface-treated with the hybrid represented by formula 1; and,
   b: results on the chip surface-treated with the hybrid represented by the formula 2.

The chemical modification herein can be achieved by different Diels-Alder reaction substrates including photoreactive functional group, thiol specific functional group (maleimide, etc), biotin, NTA (nitrilotetra-acetic acid), IDA (iminodiacetic acid), maltose or specific reactive functional group (diene, dienophile), etc. The peptide hybrid for protein immobilization of the invention can be further applied to additional protein binding or conjugation of a specific bioactive substance through the chemical modification. This chemical modification also facilitates the development of an antibody therapeutic agent, precisely the modified peptide hybrid is acting as a carrier to deliver a therapeutic agent such as a specific compound, a bioactive peptide and a protein or a radioisotope to target region such as cancer cells. In a preferred embodiment of the invention, the peptide hybrid for protein immobilization of the present invention is used for antibody immobilization with different binding capacities according to their origins or subtypes, when the target protein is an antibody. The peptide hybrid represented by formula 1 can be strongly bound to human and rabbit originated antibodies (see FIG. 2a) and the peptide hybrid represented by formula 1a can be particularly strongly bound to human originated HIgG1 ($K_d$=85 nM) and HIgG2 and rabbit originated IgG ($K_d$=305 nM) (see FIGS. 3 and 4).

The present invention also provides a method for preparing a protein monolayer comprising the following steps:

1) activating the carboxyl group included in a solid substrate;

2) surface-treating the solid substrate of step 1) with the peptide hybrid for protein immobilization of the invention; and, 3) binding a protein onto the surface-treated solid substrate of step 2), and a substrate for protein immobilization surface-treated with the peptide hybrid for protein immobilization of the invention prepared by the same.

The solid substrate above can be selected from the group consisting of CM-5 Au sensor chip, magnetic micro beads, glass plate, gold nano particles, biodegradable organic polymer nano particles such as PLGA or various (micro) well plates. The solid substrate characteristically contains a carboxyl group and once this carboxyl group is activated it will be reacted with the terminal amine group of the peptide hybrid for protein immobilization of the invention to immobilize the hybrid. The surface-treatment on a solid substrate facilitates the protein binding with controlled orientation and increases the surface regularity of the solid substrate. According to the preparing method of a monolayer using the peptide hybrid for protein immobilization of the present invention, particularly when the protein herein is an antibody, physical and chemical stability is improved, compared with the conventional method using an antibody binding protein (protein A, protein G, protein A/G or protein L), various chemical modifications are allowed with extending the range of applications, and antibody selection and binding capacity are also increased compared with the conventional method using a low molecular weight compound.

The hybrid is preferably one of the peptide hybrids for protein immobilization represented by formulas 1-3 comprising the peptide having the amino acid sequence selected from the group consisting of sequences represented by SEQ. ID. NO: 1-NO: 5 and formula 4 shown in Table 1, and is more preferably the peptide hybrid for protein immobilization represented by formula 1a comprising the peptide having the amino acid sequence represented by SEQ. ID. NO: 4.

The antibody is human, rabbit, mouse or goat originated immunoglobulin G. If the substrate is treated with the peptide hybrid for protein immobilization represented by formula 1a, the antibody is preferably human or rabbit originated immunoglobulin G.

The various solid substrate surfaces-treated according to the method of the invention can be effective in variety of antibody immobilization. Human-originated and rabbit-originated IgGs are immobilized effectively on all of the CM-5 Au sensor chip surface-treated with the peptide hybrid for protein immobilization of the invention represented by formula 1a (see FIGS. 2-6), magnetic micro beads (see FIG. 7) and glass plate (see FIG. 8). In the meantime, mouse-originated and goat originated IgGs are not successfully immobilized thereon. The method of the invention is also useful for the construction of a biosensor based on micro particles and the glass plate surface-treated according to the method of the invention has been confirmed to maintain its antibody binding capacity after several months storage at room temperature.

The present invention further provides an immunosensor having an antibody immobilized on its solid substrate surface via the peptide hybrid of the invention.

Anti-CRP antibody was immobilized on the chip surface-treated with the peptide hybrid for protein immobilization of 1a, and then antigen-antibody binding was measured with spilling the antigen CRP by surface plasmon resonance (SPR). As a result, it was confirmed that the anti-CRP antibody was bound to the antigen CRP (see FIG. 5). The surface of the chip treated with the peptide was so stable that the antibody binding capacity was not reduced after washing the surface with 20 mM NaOH and reusing it for the antibody-antigen binding.

The antigen-antibody binding capacity was compared between the anti-CRP antibody chip surface-treated with the peptide hybrid for protein immobilization of 1a and the anti-CRP antibody chip chemically treated. As a result, the binding capacity of the chip with anti-CRP-antibody immobilized on its surface by using the peptide hybrid of 1a was approximately 1.6 fold higher than that of the chip with anti-CRP antibody immobilized by the chemical treatment (see FIG. 6).

The present invention also provides a detection method of an antigen comprising the step of detecting the antigen-antibody reaction after adding a sample antigen to the antibody immobilized on the immunosensor.

The immunosensor can be prepared by the steps of surface-treating a solid substrate having the activated carboxyl group with the peptide hybrid and fixing a target antigen specific antibody thereon.

The antigen-antibody reaction can be detected by SPR, enzyme immunoassay, and fluorescence assay using a fluorescent probe. After binding an antigen specific antibody-coloring enzyme conjugate to an antigen and washing, a substrate reacting to the coloring enzyme was added, followed by measuring the color development. The coloring enzyme is selected from the group consisting of HRP (horseradish peroxidase), GUS (β-Glucuronidase), AP (alkaline phophatase), β-Gal (β-Galactosidase) and luciferase, but not always limited thereto. Or after binding an antigen-specific antibody-fluorescent probe conjugate and washing, fluorescence was measured. The fluorescent probe is selected from the group consisting of 6-FAM, fluorescein, Cy3, Cy5 and rhodamine, but not always limited thereto.

The detection method of the antigen-antibody reaction depends on a solid substrate of the immunosensor. Particularly, if the solid substrate is CM-5 Au sensor chip, an antigen is injected on the immunosensor at regular speed, during which the antigen-antibody binding is measured by surface plasmon resonance. In case the solid substrate is magnetic micro bead, the magnetic micro bead itself is first boiled in a buffer solution and then PAGE is performed (see FIG. 7). If the solid substrate is glass plate, the peptide surface is treated with the antibody-fluorescent probe conjugate and then fluorescence from the antibody is measured (see FIG. 8).

In addition, the present invention provides a detection method of an antibody in the sample, comprising the following steps:

1) adding an antigen binding specifically to the antibody immobilized on the immunosensor and washing thereof;
2) adding a sample to the washed immunosensor of step 1) and washing thereof; and,
3) detecting the antigen-antibody reaction between the added antigen and the immobilized antibody.

In step 3), the antigen-antibody reaction can be detected by SPR, enzyme immunoassay, and fluorescence assay using a fluorescent probe. In this step, the secondary antibody-coloring enzyme conjugate is bound to the antibody immobilized thereon, which is washed. Then, a substrate reacting to the coloring enzyme is added, followed by measuring the color development. The coloring enzyme is selected from the group consisting of HRP (horseradish peroxidase), GUS (β-Glucuronidase), AP (alkaline phophatase), β-Gal (β-Galactosidase) and luciferase, but not always limited thereto. In step 3), the reaction can also be detected by the following steps; the secondary antibody-fluorescent probe conjugate is bound to the antibody immobilized thereon, which is washed and proceeds to the measurement of fluorescence. The fluorescent probe is selected from the group consisting of 6-FAM, fluorescein, Cy3, Cy5 and rhodamine, but not always limited thereto.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Peptide Hybrid

The present inventors prepared the peptide hybrid for protein immobilization from the peptide hybrids represented by formulas 1-3 comprising the peptide containing the amino acid sequence selected from the group consisting of the sequences represented by SEQ. ID. NO: 1-NO: 5 and formula 4 shown in Table 1.

The peptides having the amino acid sequence selected from the group consisting of the sequences represented by SEQ. ID. NO: 1-NO: 5 and formula 4 (SEQ. ID. NO: 1: DDDC*AWHLGELVWC*T; SEQ. ID. NO: 2: DEDC*AWHLGELVWC*T; SEQ. ID. NO: 3: EEDC*AWHLGELVWC*T; SEQ. ID. NO: 4: EDDC*AWHLGELVWC*T; formula 4: $(RTY)_4K_2KG$; SEQ. ID. NO: 5: GHWRGWVS, C*: disulfide bond) are known to be bound to Fc region of human immunoglobulin G (DeLano W L et al., *Science* 287:1279-1283, 2000; Yang H et al., *J Peptide Res* 66(Suppl. 1):120-137, 2006; Fassina G et al., *J Mol Recognit* 11:128-133, 1998). To improve solubility of the hybrid in water-based buffer and to provide enough space in between the solid substrate and the peptide having the amino acid sequence selected from the group consisting of sequences represented by SEQ. ID. NO: 1-NO: 5 and formula 4 for effective antibody binding, the peptide hybrid was designed to have PEG (poly ethylene glycol). The designed peptide hybrid was prepared by solid phase synthesis. The product with 97% purity confirmed by HPLC was purchased from BioFuture (Korea) and mass analysis was performed by MALDI-TOF to confirm the structure.

<Formula 1>

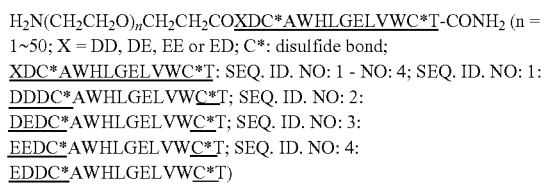

<Formula 1a>

-continued

<Formula 2>

(RTY)$_4$K$_2$KGNHCH$_2$CH$_2$(OCH$_2$CH$_2$)$_n$OCH$_2$CH$_2$2O-Cys-NH$_2$ (n = 1~50; (RTY)$_4$K$_2$KG: formula 4)

<Formula 3>

H$_2$NGHWRGWVS-NH(CH$_2$CH$_2$O)$_n$CH$_2$CH$_2$CO-Cys-NH$_2$ (n = 1~50; GHWRGWVS: SEQ. ID. NO: 5)

<Formula 4>

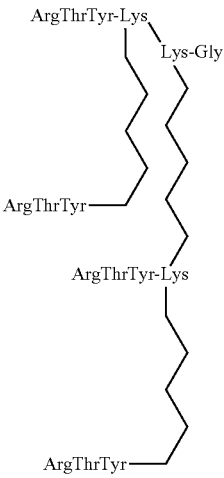

TABLE 1

Peptide hybrid for protein immobilization

| No | Formula | | Amino acid sequence |
|---|---|---|---|
| 1 | H$_2$N(CH$_2$CH$_2$O)$_n$CH$_2$CH$_2$COXDC*AWH LGELVWC*T-CONH$_2$ | SEQ. ID. NO: 1<br>SEQ. ID. NO: 2<br>SEQ. ID. NO: 3 | DDDC*AWHLGELVWC*T<br>DEDC*AWHLGELVWC*T<br>EEDC*AWHLGELVWC*T |
| 1a | H$_2$N(CH$_2$CH$_2$O)$_2$CH$_2$CH$_2$COEDDC*AW HLGELVWC*T-CONH$_2$ | SEQ. ID. NO: 4 | EDDC*AWHLGELVWC*T |
| 2 | (RTY)$_4$K$_2$KGNHCH$_2$CH$_2$(OCH$_2$CH$_2$)$_n$ OCH$_2$CH2$_2$O-Cys-NH$_2$ | Formula 4 | (RTY)$_4$K$_2$KG |
| 3 | H$_2$NGHWRGWVS-NH(CH$_2$CH$_2$O)nCH$_2$CH$_2$CO-Cys-NH$_2$ | SEQ. ID. NO: 5 | GHWRGWVS |

C*: disulfide bond

Example 2

Preparation of Antibody Samples and Reagents

Various immunoglobulin Gs having different isotypes and origins from human (HIgG1, HIgG2 and HIgG3), rabbit, mouse (MIgGA, MIgG1, MIgG2 and MIgG3) and goat, were purchased from Sigma-Aldrich (USA) along with (3-aminopropyl)trimethoxysilane (APTS), N-hydroxysuccinimide (NHS), 1-ethyl-3-(3-dimethylaminopropyl)carbodiimide (EDC), 2-(N-morpholino)ethanesulfonic acid (MES), ethanolamine and Succinic anhydride-DMF, etc used for the antibody labeling. C-reactive protein (CRP) and rabbit anti-CRP antibody were purchased from Calbiochem (USA). Cys-mono NHS ester used for the antibody labeling was purchased from GE Healthcare (Korea). CM-5 Au sensor chip for the measurement of surface plasmon resonance was purchased from Biacore AB (Sweden), magnetic micro beads (Dynabeads MyOne™ Carboxylic Acid) were purchased from DYNAL (USA), and the glass plate was purchased from Corning (Korea).

Example 3

Antibody Binding Capacity of the Peptide Hybrid for Protein Immobilization Immobilized on the Dextran Chip with Controlled Orientation <3-1> Immobilization of the Peptide Hybrid with Controlled Orientation The peptide hybrid for protein immobilization prepared in Example 1 was immobilized on a solid substrate having a carboxyl group on its surface.

PBS containing 0.2 M EDC and 0.05 M NHS was spilled on the dextran CM-5 Au sensor chip (Biacore AB, Sweden) at the speed of 7 μl/minute to activate the carboxyl group on the surface of the sensor chip. Then, PBS containing 100 μM of the peptide hybrid was spilled thereon at the same speed for 30 minutes. The peptide hybrid was bound to the surface via the reaction of the terminal amine group on the sensor chip activated as NHS ester form. The surface area remaining non-reacted with the peptide hybrid was inactivated by using 1 M of ethanolamine solution (pH 8.5).

<3-2> Measurement of Antibody Binding Capacity

The chip surface-treated with the peptide hybrid for protein immobilization prepared in Example <3-1> was bound to the antibody of Example 2.

Antibody solutions containing different animal originated antibodies of Example 2 or 5 μg/ml of BSA (control) in PBS were spilled on the chip of Example <3-1> at the speed of 10 μl/minute to bind the antibody to the peptide hybrid on the surface of the chip. The binding capacity was measured by surface plasmon resonance (SPR) using Biacore 3000.

As a result, the peptide hybrid for protein immobilization represented by formula 1 was strongly attached to the different types of antibodies (FIG. 2a), while the peptide hybrids for protein immobilization represented by formulas 2-3 exhibited low reaction values of up to 200 RU (FIG. 2b).

In particular, the peptide hybrid represented by formula 1a (wherein, n=2 and x=ED) (hereafter, hybrid of 1a) was bound to the human originated IgG (HIgGs 1-3) and the rabbit originated IgG to the saturated level (12000 RU). However, the hybrid of 1a was bound to the rabbit originated antibodies (mixed composition of MIgGs 1-3) and to the goat originated antibody only at minimum level but not bound to BSA (FIG. 2a).

Figure 3:
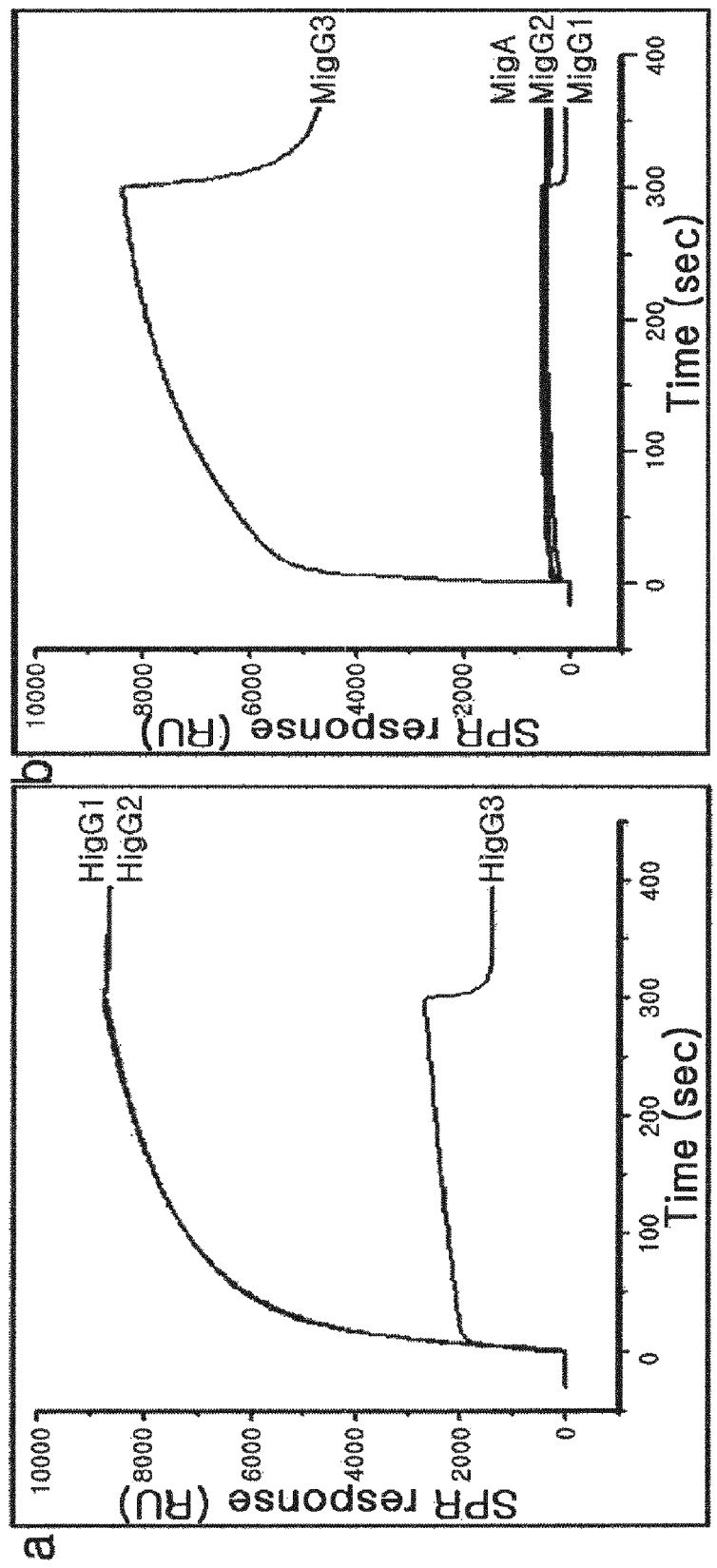
FIG. 3 is a set of graphs illustrating the binding capacities of human and mouse antibodies to the dextran CM-5 Au sensor chip surface-treated with the peptide hybrid for protein immobilization of 1a of the invention measured by surface plasmon resonance:
   a: binding capacities of human antibodies HIgG1, HIgG2 and HIgG3 measured by surface plasmon resonance; and,
   b: binding capacities of mouse antibodies MIgGA, MIgG1, MIgG2 and MIgG3 measured by surface plasmon resonance.
Figure 4:
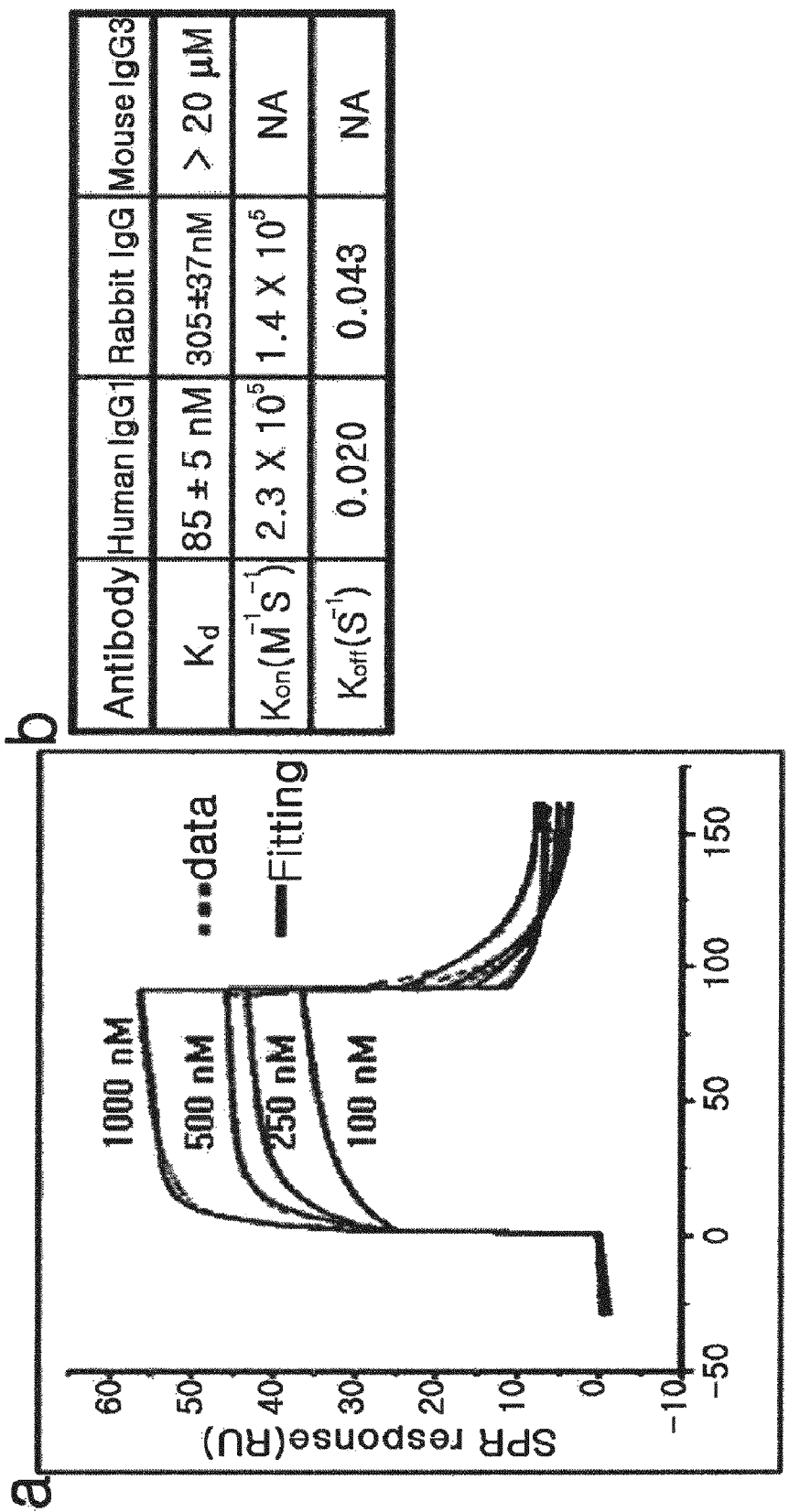
FIG. 4 is a graph illustrating the binding affinity between the peptide hybrid of 1a and human, rabbit, mouse and goat antibodies:
   a: binding capacity of human IgG1 (anti CRP) antibody (100 nM, 250 nM, 500 nM and 1,000 nM) to the dextran CM-5 Au sensor chip surface-treated with the peptide hybrid for protein immobilization of 1a of the invention measured by surface plasmon resonance; and
   b: binding affinity between the peptide hybrid for protein immobilization of 1a of the invention and HIgG1, rabbit IgG and MIgG3 antibodies.

The hybrid of 1a was effectively bound to the human originated HIgG1 and HIgG2, but barely bound to HIgG3 (FIG. 3). The hybrid was bound to the mouse originated antibody MIgG3 to some degree but hardly bound to MIgGA, MIgG1 and MIgG2 (FIG. 3b).

<3-3> Binding Affinity of the Hybrid of 1a

Binding affinity of the hybrid of 1a confirmed to have antibody binding capacity in Examples <3-1> and <3-2> to the antibody was measured.

The antibody solutions containing HIgG1, rabbit IgG, MIgG3 antibodies at the concentrations of 100 nM, 250 nM, 500 nM and 1,000 nM were spilled on the chip surface-treated with the hybrid of 1a of Example <3-1> at the speed of 10 µl/minute to induce the binding reaction and the degree of binding was measured by surface plasmon resonance (SPR) using Biacore 3000.

As a result, SPR sensor gram values represented in dotted line were obtained. The values were analyzed by nonlinear regression using BIAevaluation software equipped in Biacore 3000 to draw a theoretical line graph (FIG. 4a). From the theoretical graph, kinetic coefficients shown in FIG. 4b were obtained and the overlapping of each dotted line on the line indicates the calculation was correct.

It was confirmed that the hybrid of 1a was strongly bound to the human originated HIgG1 ($K_d$=85 nM) but it had low binding affinity to the rabbit originated IgG ($K_d$=305 nM) (FIG. 4b). Therefore, the hybrid of 1a was very useful for the antibody immobilization on the surface of a chip under the control of binding degree of different antibodies having different origins or different isotypes.

Example 4

Antigen-Binding Capacity of the Antibody Immobilized on the Chip by the Peptide Hybrid for Protein Immobilization of 1a The antigen-binding capacity of the antibody immobilized by the hybrid of 1a was measured.

<4-1> Antigen-Antibody Binding

PBS containing rabbit anti-CRP antibody at the concentration of 5 µg/ml was spilled on the chip surface-treated with the peptide hybrid of 1a prepared in Example <3-1> at the speed of 10 µl/minute for antibody immobilization. Then, PBS containing CRP at the same concentration as the above was spilled thereon, followed by measuring the antigen-antibody binding by surface plasmon resonance (SPR) using Biacore 3000. The surface of the chip was recovered by 20 mM NaOH solution for the repeat of the experiment to measure the antigen-antibody binding.

Figure 5:
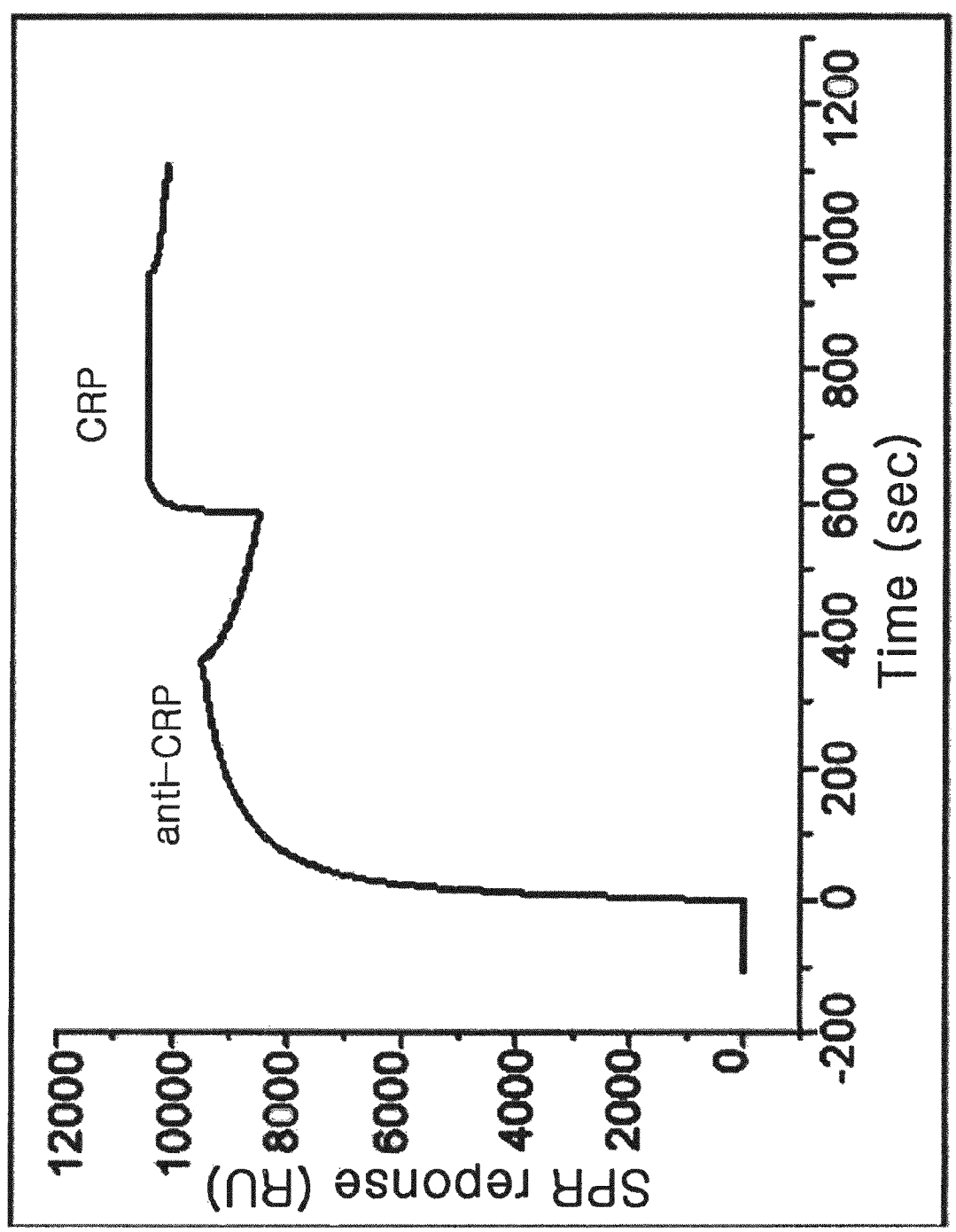
FIG. 5 is a graph illustrating the antigen binding capacity of the antibody immobilized to the dextran CM-5 Au sensor chip surface-treated with the peptide hybrid for protein immobilization of 1a of the invention.

As a result, anti-CRP antibody was very well bound to the corresponding antigen CRP (FIG. 5). Besides, the surface treated with the peptide was so stable even after washing with 20 mM NaOH solution that it could be recycled for further antigen-antibody binding reaction without reducing the antibody binding capacity.

<4-2> Antigen-Antibody Binding Under the Controlled Orientation

A buffer containing 0.2 M EDC and 0.05 M NHS was spilled on the dextran CM-5 Au sensor chip (BIacore AB, Sweden) at the speed of 7 µl/minute to activate carboxyl group on the surface of the sensor chip. Then, PBS containing 5 µg/ml of anti-CRP antibody was spilled thereon for 30 minutes at the same speed. The antibody was bound via the reaction of the terminal amine group with the carboxyl group on the sensor chip activated as NHS ester form. The surface not reacted with the antibody was inactivated by using 1 M ethanolamine solution (pH 8.5).

PBS containing 5 µg/ml of CRP was spilled on the anti-CRP antibody chip with the chemical immobilization and the anti-CRP antibody chip with the immobilization by the peptide hybrid of 1a respectively at the speed of 10 µl/minute, followed by measuring the degree of antigen-antibody binding by surface plasmon resonance using Biacore 3000.

Figure 6:
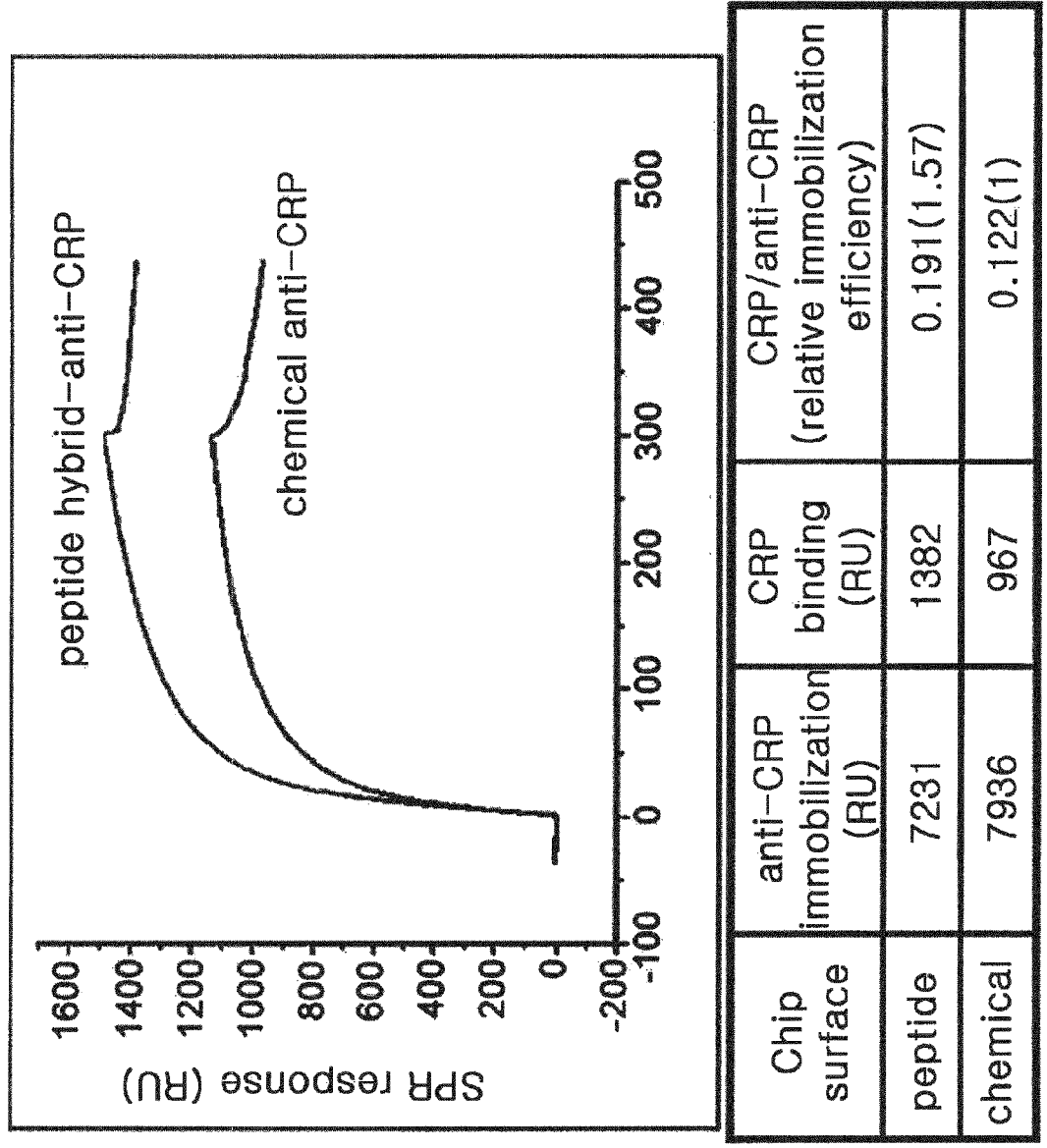
FIG. 6 is a graph illustrating the comparison of antigen-antibody binding capacity between the anti-CRP antibody chip (peptide hybrid-anti-CRP) immobilized on the chip surface-treated with the peptide hybrid of 1a of the invention and the anti-CRP antibody chip (chemical anti-CRP) immobilized on the surface of the chip by chemical method.

As a result, the binding capacity was approximately 1.6 fold higher on the chip having anti-CRP antibody immobilized on the surface by the peptide hybrid of 1a than on the chip having anti-CRP antibody immobilized on its surface by the conventional chemical method (FIG. 6).

Example 5

Antibody Binding Capacity of the Peptide Hybrid for Protein Immobilization of 1a Immobilized on Magnetic Micro Beads with Controlled Orientation <5-1> Immobilization of the Peptide Hybrid of 1a with Controlled Orientation The peptide hybrid for protein immobilization of 1a obtained in Example 1 and confirmed to have antibody binding capacity in Example 3 was immobilized on the surface of the magnetic micro bead having a carboxyl group on its surface.

The surface of the magnetic micro bead containing a carboxyl group was activated by loading 25 mM of MES (pH 6) containing NHS (0.4 M) and EDC (0.2 M). Only magnetic micro bead was recovered by using a magnet and the activated magnetic micro bead was reacted with 0.2 mg/ml of the peptide hybrid of 1a at room temperature for one hour. The activated magnetic micro bead was reacted with PBS alone for the control group. Non-reacted active ester group was inactivated by using 1 M of ethanolamine (pH 8.5). Both the magnetic micro bead with the peptide hybrid of 1a attached and the magnetic micro bead without the peptide hybrid of 1a were repeatedly washed by PBS and diluted in PBS (final concentration: 5 mg/ml).

<5-2> Antibody Binding Capacity

To confirm the binding of the magnetic micro bead adhered with the peptide hybrid of 1a to the antibody, 2 mg/ml (final concentration) of the magnetic micro bead and 0.1 mg/ml of the antibody used in Example <3-2> were mixed to induce binding reaction. After inducing reaction for one hour at room temperature, the magnetic micro bead was dragged down to the bottom of the vessel by using a magnet and the supernatant was eliminated. This process was repeated five times to remove the non-reacted antibodies. The magnetic micro bead reacted with the antibody was added in PAGE loading buffer containing a reducing agent (2-mercaptoethanol), which was heated to separate the antibody chain from the magnetic micro bead, followed by PAGE.

The antibody bound to the magnetic micro bead was quantified by using 12% polyacrylamide gel containing 10% SDS. Particularly, 20 µl of PBS containing 2% micro bead was mixed with 5 µl of sample buffer (pH 6.8; 60 mM Tris-HCl, 25% glycerol, 2% SDS, 14.4 mM 2-mercaptoethanol, 0.1% bromophenol blue, $H_2O$), followed by heating at 90° C. for 10 minutes. 15 µl of the sample was placed on each well of polyacrylamide gel. 200 V of voltage was applied thereto at room temperature for one hour to migrate sample, followed by dipping the gel in the staining solution (0.5% coomassie blue, 45% methanol, 10% acetic acid solution) at room temperature for 30 minutes. Upon completion of staining, the gel was transferred into the destaining solution (10% methanol, 10% acetic acid solution), followed by stirring at room temperature for 3 hours. The excessive staining reagent was eliminated by washing.

Figure 7:
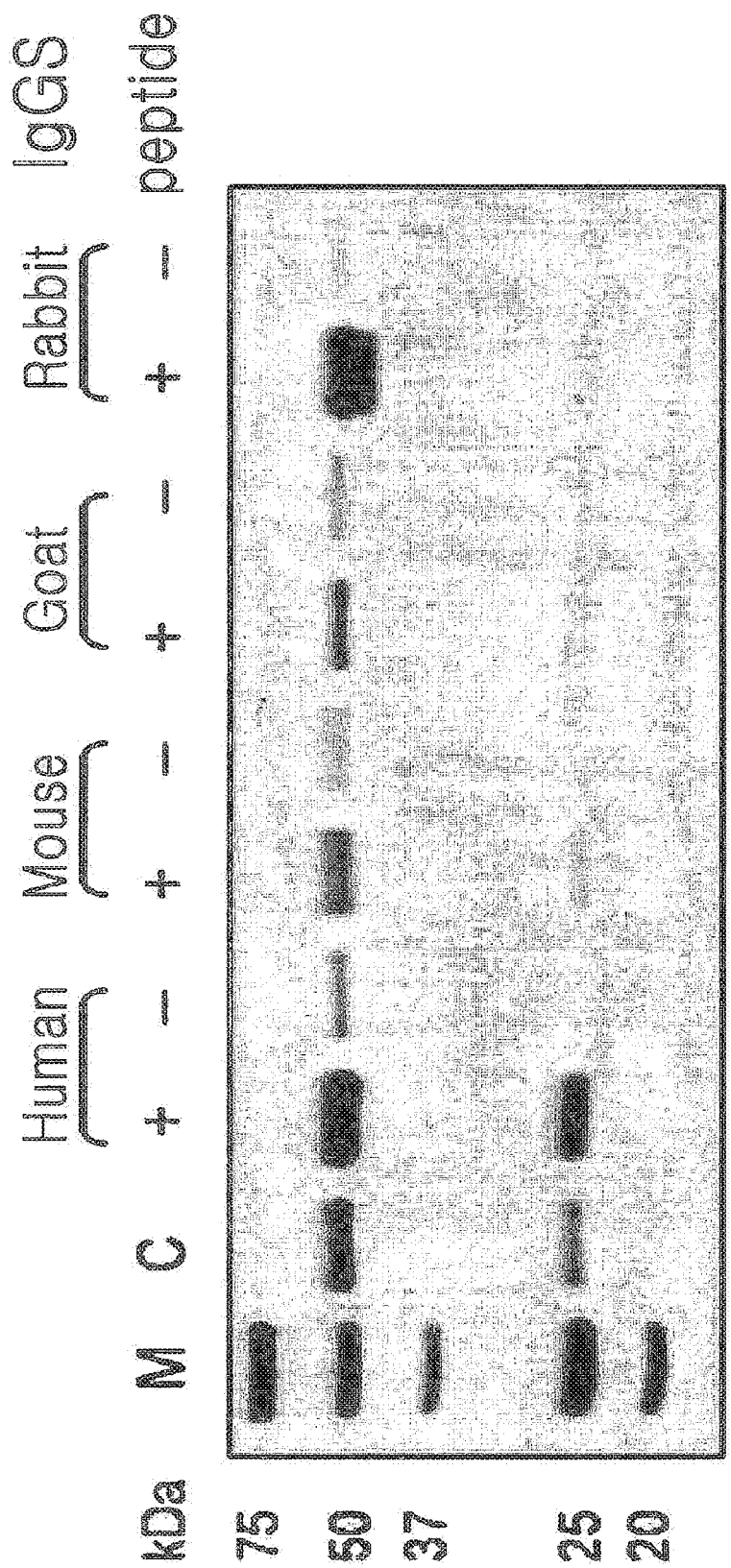
FIG. 7 is a photograph illustrating the binding capacities of human, mouse, goat and rabbit antibodies to the magnetic micro beads surface-treated with the peptide hybrid of 1a of the invention measured by PAGE.

As a result, after several times of washing with PBS, the antibody binding was still observed on the magnetic micro bead surface-treated with the peptide hybrid of 1a (FIG. 7). The magnetic micro bead treated with the peptide hybrid of 1a was effectively bound to the human originated HIgG and the rabbit originated IgG, but not to the mouse and goat originated IgGs, which was consistent with the result of Example 3.

Example 6

Antibody Binding Capacity of the Peptide Hybrid for Protein Immobilization of 1a Immobilized on Glass Plate with Controlled Orientation The antibody binding capacity of the peptide hybrid for protein immobilization of 1a was measured.

<6-1> Immobilization of the Peptide Hybrid of 1a with Controlled Orientation

The glass plate was treated with a mixed solution of 95% sulfuric acid and 5% hydrogen peroxide (V/V 3:1) at 60° C. for 30 minutes, followed by washing with distilled water and ethanol. The washed glass plate was soaked in 1% APTS, followed by reaction for 4 hours at room temperature to introduce amine group. The amine group introduced glass plate was reacted in 1 M succinic anhydride-DMF solution at 37° C. for 4 hours to generate carboxyl group on the glass plate. The glass plate was washed with distilled water and ethanol and dried using nitrogen gas and then stored in a vacuum drier. The carboxyl group introduced glass plate was treated with a mixed solution of 0.1 M EDC and 0.025 M NHS for 15 minutes to activate its surface. The activated glass plate was washed with distilled water and dried using nitrogen gas. The peptide hybrid for protein immobilization of 1a was dissolved in PBS containing 40% glycerol at the final concentration of 0.5 mg/ml, which was dropped on the glass plate by 1 µl per each drop, followed by reaction for 2 hours. The non-reacted active ester remaining on the glass plate was inactivated by using 1 M of ethanolamine (pH 8.5) and washed with PBS.

<6-2> Antibody Binding Capacity

The antibody binding capacity of the glass plate surface-treated with the hybrid of 1a was measured by using Cy3 labeled antibodies.

First, 5 µl of 3.34 mM Cy3-mono NHS ester-DMF solution was added into 100 µl of each PBS respectively containing HIgG (mixture of HIgG 1-HIgG 3), MIgG (mixture of MIgG 1-MIgG 3), rabbit IgG and goat IgG (0.5 mg/ml), followed by reaction for 30 minutes at room temperature. Then the mixture proceeded to mini-gel column (PD-10 desalting column, Armersham-Biosceince, USA) to eliminate excessive fluorescent dye and filtered protein was used for the experiment. The antibodies labeled with Cy3 were diluted in PBS containing 0.01% Tween 20 and 0.1 µg/ml BSA at the final concentration of 1 g/ml.

The Cy3 labeled antibody solution was dropped on the glass plate surface-treated with the hybrid of 1a by 50 µl per each drop, followed by reaction for one hour at room temperature. The glass plate was washed with PBST, PBS and distilled water in that order and dried using nitrogen gas, followed by observation of fluorescent images on the glass plate using GenPix 4200 (Axon, USA) camera.

Figure 8:
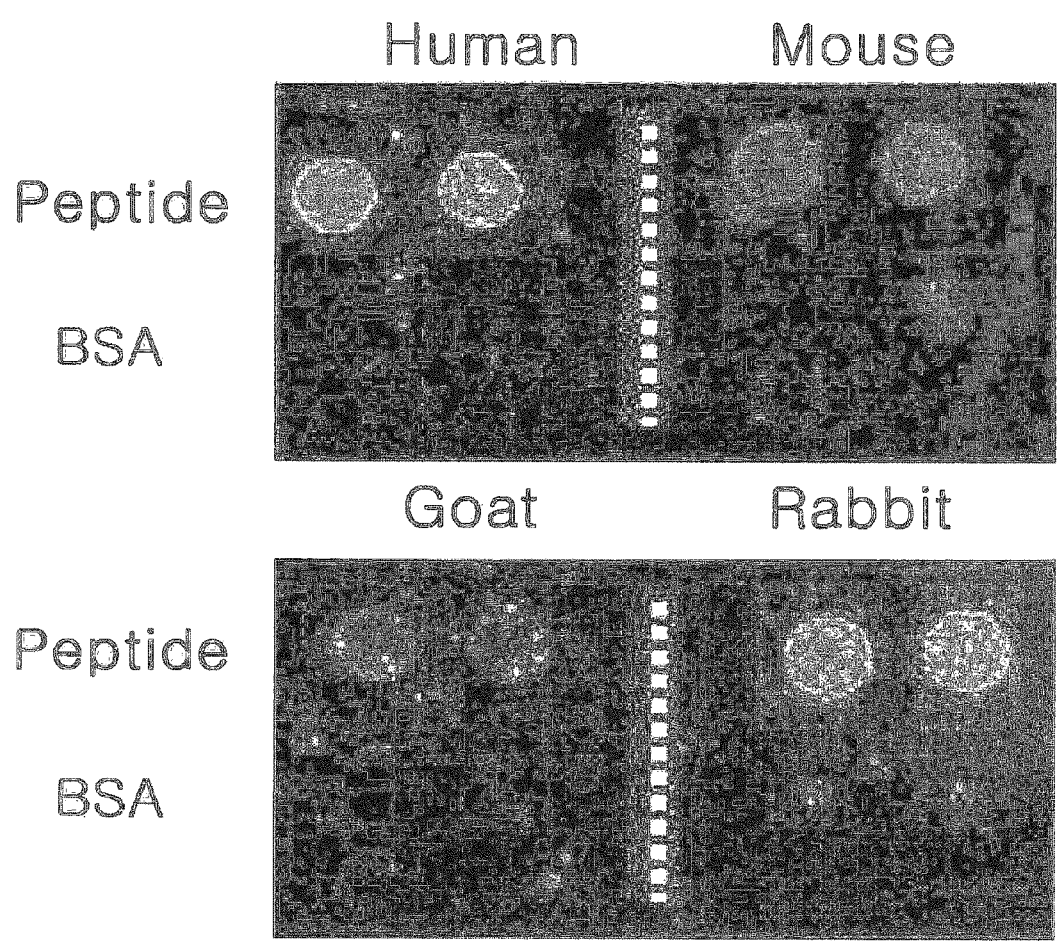
FIG. 8 is a set of photographs illustrating the binding capacities of human, mouse, goat and rabbit antibodies to the glass plate surface-treated with the peptide hybrid of 1a of the invention measured by PAGE.

As a result, the human originated and rabbit originated antibodies were bound very well to the glass plate surface-treated with the hybrid of 1a, while the mouse originated and goat originated antibodies were not bound well to the glass plate (FIG. 8).

Even after several months storage at room temperature, the glass plate surface-treated with the hybrid of 1a maintained its antibody binding capacity, suggesting that the surface treatment was very successfully performed providing very stable surface structure.

INDUSTRIAL APPLICABILITY

As explained hereinbefore, the peptide hybrid for protein immobilization of the present invention provides orientation to an antibody on various types of solid substrate surfaces and facilitates the immobilization of antibodies having different affinities according to their origins or subtypes. Thus, the surface treatment technique using the peptide hybrid of the invention can be effectively used for the production of various immunosensors and immune chips.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A peptide hybrid for antibody immobilization, wherein the hybrid is represented by Formula 1:

<Formula 1>

H$_2$N(CH$_2$CH$_2$O)$_n$CH$_2$CH$_2$COXDC*AWHLGELVWC*T-CONH$_2$ wherein, (n = 1~50; X = DD, DE, EE or ED;
C*: disulfide bond; and
XDC*AWHLGELVWC*T is selected from the group consisting of SEQ. ID. NO: 1, SEQ. ID. NO: 2, SEQ. ID. NO: 3, and SEQ. ID. NO: 4.

2. The peptide hybrid for antibody immobilization according to claim 1, wherein X=ED; and EDDC*AWHLGELVWC*T: SEQ. ID. NO: 4.

3. A substrate for antibody immobilization surface-treated with the peptide hybrids for antibody immobilization of claim 1.

4. An immunosensor having an antibody immobilized via the hybrid on solid substrate surface-treated with the hybrids for antibody immobilization of claim 1.

5. A method for improving solubility of an oligopeptide and orienting an antibody by conjugating an oligopeptide to a polymer to provide a peptide hybrid for antibody immobilization, wherein the peptide hybrid is represented by Formula 1:

<Formula 1>

H$_2$N(CH$_2$CH$_2$O)nCH$_2$CH$_2$COXDC*AWHLGELVWC*T-CONH$_2$
wherein, n = 1~50; X = DD, DE, EE or ED;
(C*: disulfide bond; and XDC*AWHLGELVWC*T is
selected from the group consisting of
SEQ. ID. NO: 1, SEQ. ID. NO: 2, SEQ. ID. NO: 3,
and SEQ. ID. NO: 4).

6. The method according to claim 1, wherein X=ED; and EDDC*AWHLGELVWC*T: SEQ. ID. NO: 4.

* * * * *